US00PP28211P3

(12) United States Plant Patent
Olsthoorn

(10) Patent No.: US PP28,211 P3
(45) Date of Patent: Jul. 18, 2017

(54) ***SPATHIPHYLLUM* PLANT NAMED 'SWEET GINO'**

(50) Latin Name: ***Spathiphyllum* Schott**
Varietal Denomination: Sweet Gino

(71) Applicant: Petrus Olsthoorn, Honselersdijk (NL)

(72) Inventor: Petrus Olsthoorn, Honselersdijk (NL)

(73) Assignee: P.C.M. Oslthoorn Holding B. V., Honselersdijk (NL)

( * ) Notice: Subject to any disclaimer, the term of this patent is extended or adjusted under 35 U.S.C. 154(b) by 34 days.

(21) Appl. No.: 14/756,910

(22) Filed: Oct. 28, 2015

(65) Prior Publication Data

US 2016/0150710 P1 May 26, 2016

(30) Foreign Application Priority Data

Nov. 25, 2014 (QZ) ..... 2014/2770

(51) Int. Cl.
*A01H 5/02* (2006.01)

(52) U.S. Cl.
USPC ..... Plt./364

(58) Field of Classification Search
USPC ..... Plt./364
See application file for complete search history.

*Primary Examiner* — Keith Robinson
(74) *Attorney, Agent, or Firm* — Samuel R. McCoy, Jr.

(57) ABSTRACT

'Sweet Gino' is a new and distinctive variety of *Spathiphyllum* which is characterized by large and attractive flowers presented at or slightly above the foliage, a relative abundance of fully opened flowers, dark green and glossy foliage with unruffled margins, and the stability of all characteristics from generation to generation. The new variety is typically produced as an indoor ornamental plant.

3 Drawing Sheets

Latin name of the genus and species: The Latin name of the genus and species of the novel variety disclosed herein is *Spathiphyllum* Schott.

Variety denomination: The inventive variety of *Spathiphyllum* disclosed herein has been given the variety denomination 'Sweet Gino'.

CROSS REFERENCE TO RELATED APPLICATIONS

This application claims priority to the Community Plant Variety Rights application number 2014/2770, filed Nov. 25, 2014, which is herein incorporated by reference.

BACKGROUND OF THE INVENTION

The present invention relates to a new and distinct cultivar of *Spathiphyllum*, which has been given the variety denomination of 'Sweet Gino'. Its market class is PLT/364.

Parentage: The new cultivar is a seedling selection which resulted from the controlled pollination of the seed parent, an unnamed, unpatented internal breeding line identified only as '04081-1', and the pollen parent, an unnamed, unpatented internal breeding line identified as '04094-1', during the spring of 2008. Both parents are developed and owned by the inventor and were never commercially released or assigned variety names and are only identified by the aforementioned breeding codes. Said cross was performed by the inventor at a commercial greenhouse in Honselersdijk, The Netherlands during the spring of 2008. After approximately one and a half years of evaluation, the new cultivar was selected in autumn of 2009 due to its attractive flower presentation and glossiness of the foliage. The new cultivar was given the breeder denomination 'Sweet Gino'.

Asexual Reproduction: Asexual reproduction of 'Sweet Gino', by way of tissue culture, was first performed in the autumn of 2009 at a commercial laboratory in Honselersdijk, the Netherlands. Successive generations so produced have shown that the unique features of the instant cultivar are stable and reproduced true to type.

SUMMARY OF THE INVENTION

The cultivar 'Sweet Gino' has not been observed under all possible environmental conditions and the phenotype may vary somewhat with variations in the instant environment such as temperature, day length, and light intensity, without, however, any variance in genotype. The following characteristics have been repeatedly observed and represent the distinguishing characteristics of the new *Spathiphyllum* cultivar 'Sweet Gino'. These traits, in combination, distinguish 'Sweet Gino' as a new and distinct cultivar.

1. *Spathiphyllum* 'Sweet Gino' exhibits attractive white flowers with a large spathe and spadix, presented at or slightly above the foliage; and
2. *Spathiphyllum* 'Sweet Gino' exhibits a relative abundance of fully opened flowers, in good condition, being presented simultaneously; and
3. *Spathiphyllum* 'Sweet Gino' exhibits unruffled, entire leaf margins; and.
4. *Spathiphyllum* 'Sweet Gino' exhibits dark green, glossy foliage.

Figure 1:
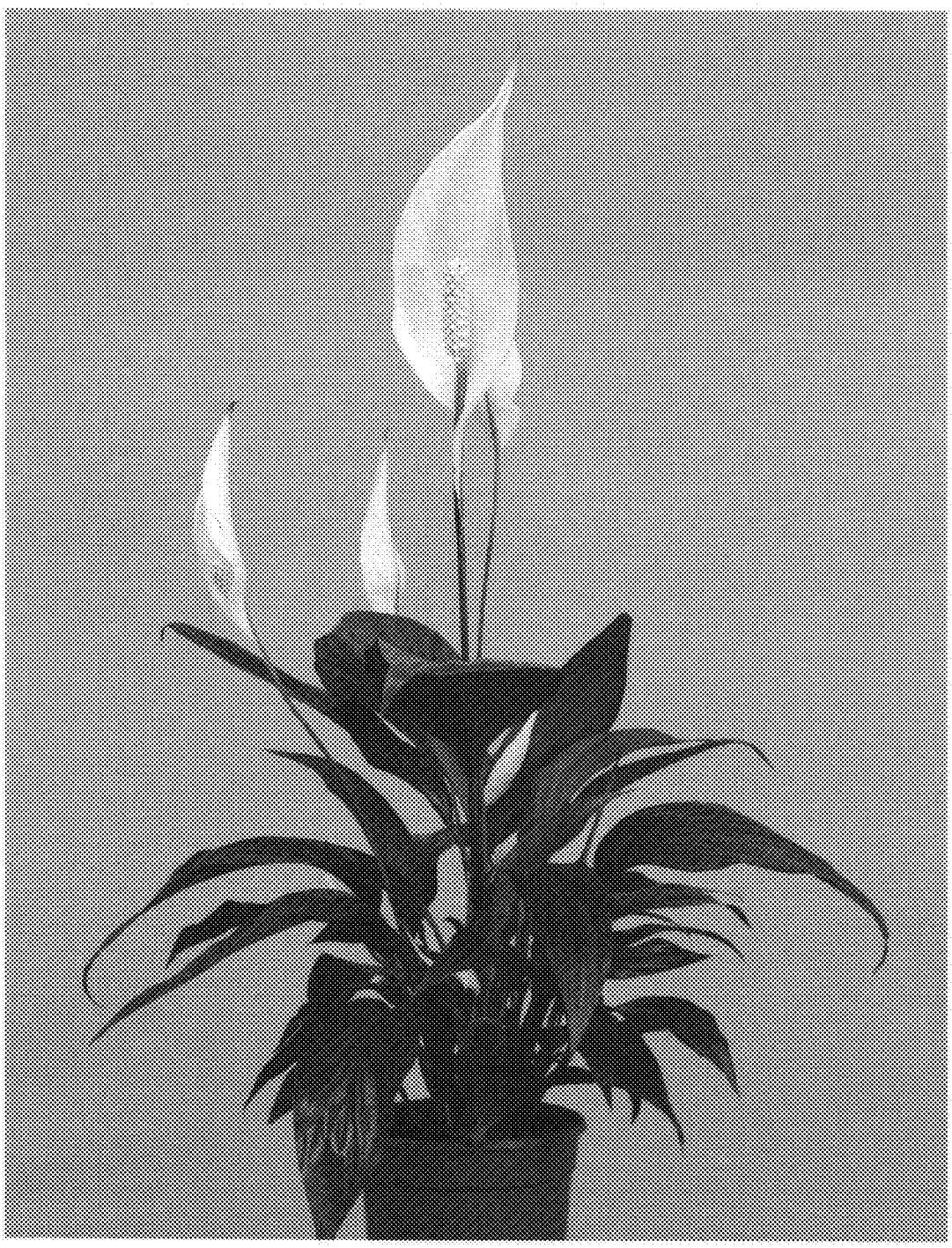
FIG. 1 shows, as nearly true as it is reasonably possible to make the same in color illustrations of this type, the typical foliage and growth characteristics of the new cultivar, 'Sweet Gino'. The plant shown is approximately 2 months old from a rooted cutting, potted into an 11 cm nursery pot, grown in a climate-controlled greenhouse in Roelofarendsveen, the Netherlands.
Figure 2:
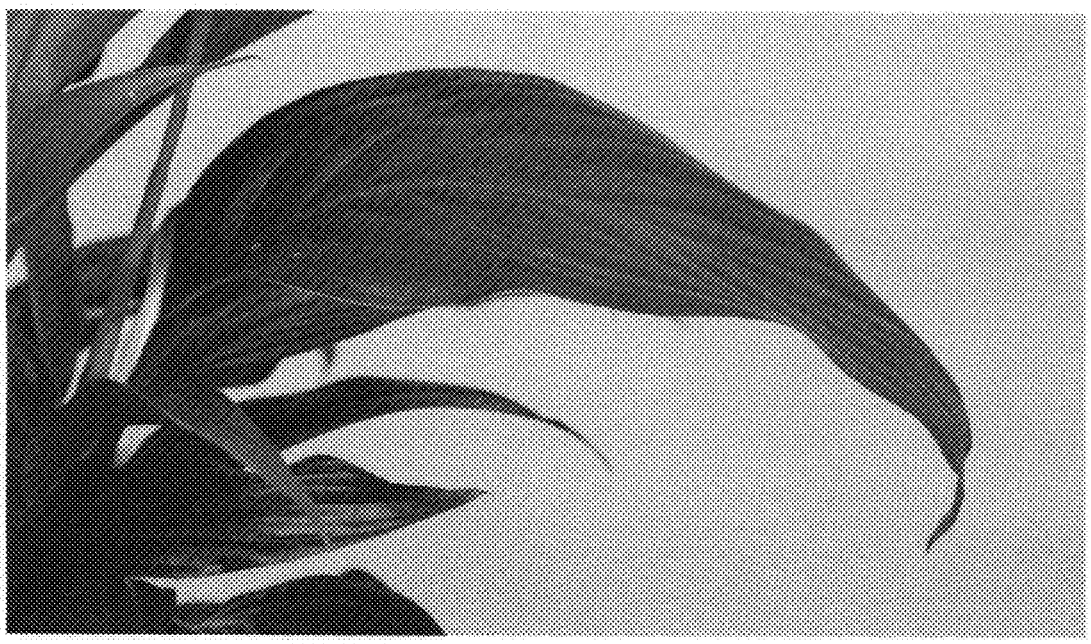
FIG. 2 shows, as nearly true as it is reasonably possible to make the same in color illustrations of this type, the typical foliage of the plant in FIG. 1.
Figure 3:
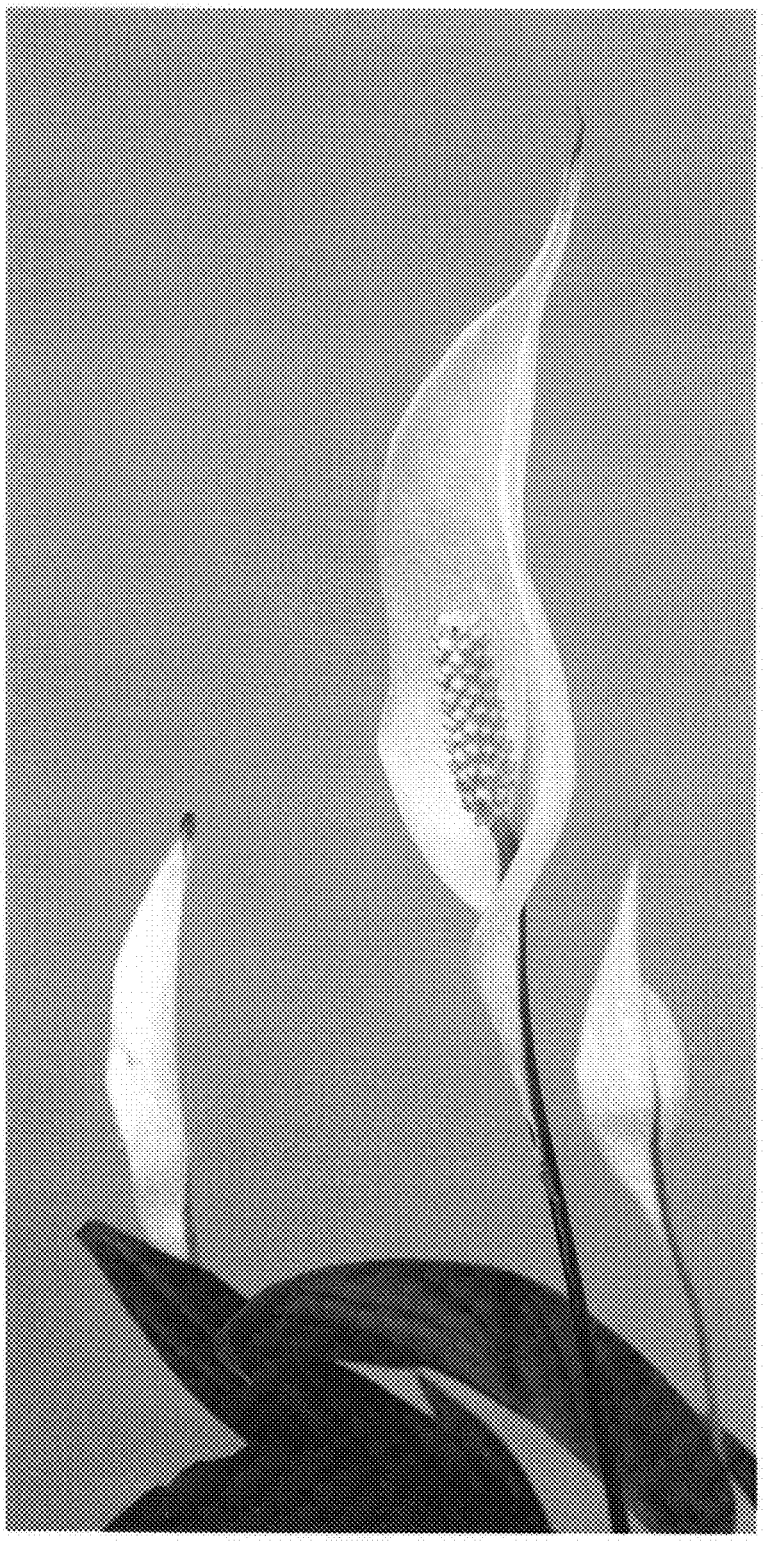
FIG. 3 shows, as nearly true as it is reasonably possible to make the same in color illustrations of this type, the typical flower of the plant in FIG. 1.

The photographs were taken using conventional techniques and although colors may appear different from actual colors due to light reflectance it is as accurate as possible by conventional photographic techniques.

BOTANICAL DESCRIPTION OF THE PLANT

The following is a detailed botanical description of a new and distinct variety of *Spathiphyllum* known as 'Sweet Gino', based upon observations of plants, approximately 24 weeks old from a rooted cutting, grown in a climate-controlled greenhouse in Roelofarendsveen, the Netherlands. Observation data was recorded in September of 2015.

Those skilled in the art will appreciate that certain characteristics will vary with older or, conversely, with younger plants. 'Sweet Gino' has not been observed under all possible environmental conditions. Where dimensions, sizes, colors and other characteristics are given, it is to be understood that such measurements are approximations or averages set forth as accurately as practicable. The phenotype of the variety may differ from the descriptions set forth herein with variations in environmental, climactic and cultural conditions. Color notations are based on *The Royal Horticultural Society Colour Chart*, The Royal Horticultural Society, London, 2007 edition.

A botanical description of 'Sweet Gino' and comparisons with the parent and the most similar variety of common knowledge are provided below.

General plant description:

*Growth rate*.—Low to moderate.

*Growth habit*.—Clump forming; upright.

*Plant shape*.—Globular with flowers sitting above the foliage.

*Height*.—32.5 cm in height, to the highest leaf; 56.1 cm to top of highest spathe.

*Width*.—Average 53.2 cm in width.

*Hardiness*.—USDA Zone 10.

*Propagation*.—Stem cuttings and tissue culture.

*Time to initiate roots*.—Approximately 14 days to initiate roots at approximately 20 to 22 degrees Centigrade.

*Time to produce a rooted cutting*.—Approximately 5 to 6 weeks at approximately 20 to 22 degrees Centigrade.

*Environmental tolerances*.—Moderately high drought tolerance once established; good heat tolerance.

*Pest resistance and susceptibility*.—Plants have not been observed to be susceptible or resistant to pathogens and pests common to *Spathiphyllum*.

Root system: Moderately fibrous, not fleshy; moderately dense; color is near RHS 159A to 15D.

Stems:

*Branching characteristics*.—Clumping plant with leaves emerging directly from the base of the plant; no lateral branching.

Foliage:

*Arrangement*.—Alternate, growing directly from the soil.

*Quantity of leaves per shoot*.—Average of 6.

*Quantity of shoots per plant*.—Average of 8.

*Quantity of leaves per plant*.—Approximately 48.

*Leaf shape*.—Narrow ovate to lanceolate.

*Leaf apex*.—Long apiculate.

*Leaf base*.—Attenuate.

*Aspect*.—Slightly carinate, slightly reflexed with an outward attitude.

*Leaf length*.—Average 25.1 cm in length.

*Leaf width*.—Average 8.3 cm in width.

*Leaf margin*.—Entire; slightly undulate.

*Texture, adaxial surface*.—Glabrous and glossy.

*Texture, abaxial surface*.—Glabrous and moderately glossy to glossy.

*Juvenile color, adaxial surface*.—In between RHS 143A and 146A.

*Juvenile color, abaxial surface*.—In between RHS 138A and 146B.

*Mature color, adaxial surface*.—In between RHS N137A and 147A.

*Mature color, abaxial surface*.—Near RHS 137B.

*Venation*.—Vein pattern — Pinnate. Vein color, adaxial surface — Near RHS 137A. Vein color, abaxial surface — Near RHS 144B.

*Petiole, excluding geniculum*.—Length — Approximately 11.8 cm. Width — Approximately 0.4 cm at the geniculum and 0.8 above clump. Color — Near RHS 143A. Strength — Moderately strong. Geniculum — Length — Approximately 2.4 cm. Width — Approximately 0.45 cm. Color — Near RHS 143B. Petiole wings — Length — Approximately 10.6 cm. Width — Approximately 0.7 cm. Color — Near in between RHS 143A and 146A.

Inflorescence:

*Type*.—Spathe.

*Arrangement*.—Spathes are carried slightly in between and above the leaf plane.

*Flowering habit*.—Continuous.

*Quantity of spathes per plant*.—On average 4 fully open spathes, in good condition.

*Natural flowering season*.—Late summer to midwinter.

*Time to flowering*.—35 weeks (natural flowering).

*Fragrance*.—Moderately strong, sweet and pleasant (typical *Spathiphyllum* scent).

*Self-cleaning or persistent*.—Persistent.

*Flower longevity*.—Flowers stay in good condition approximately 3 weeks on the plant.

*Peduncle*.—Length — Approximately 41.2 cm. Diameter — Approximately 0.3 cm at the smallest point and 0.35 cm at the widest. Color — Near RHS 143A. Strength — Moderately strong.

Spathe:

*Aspect*.—Upright.

*Length*.—Approximately 24.1 cm.

*Width*.—Approximately 6.2 cm.

*Shape*.—Ovate, concave.

*Margin*.—Entire.

*Apex*.—Narrow Apiculate.

*Base*.—Attenuate.

*Color*.—Front when opening — Near RHS NN155A and tipped nearest to RHS 146A. Back when opening — Near RHS NN155A and tipped nearest to RHS 146A; main vein RHS 143B. Front when mature — Near RHS NN155D and tipped nearest to RHS 146A. Back when mature — Near RHS NN155C and tipped nearest to RHS 146A; main vein RHS 143B. Fading to — Not fading.

Spadix:

*Shape*.—Oblong.

*Apex*.—Obtuse.

*Base*.—Obtuse.

*Length*.—Approximately 4.8 cm.

*Width*.—Approximately 1.6 cm.

*Color*.—When opening — Near RHS 157C. Mature — Near in between RHS 155A and 160D.

*Quantity of flowers per spadix*.—Approximately 100.

*Spadix flower arrangement*.—Spirally placed on spadix.

*Spadix flower diameter*.—Approximately 0.4 cm.

*Spadix flower depth*.—Approximately 0.25 cm.

Reproductive organs:

*Stamen*.—Six rudimentary anthers are placed around the ovary; colored in between near RHS 155A and 160D; pollen are moderately produced, colored near RHS 155D.

*Pistil*.—Three stigmas are placed on top of each ovary (length of ovary is equal to the spadix flower depth), stigma diameter is approximately 0.1 cm, colored near RHS NN155D. Ovaries are rounded at the tip.

Seed and fruit: Seed production has not been observed.

COMPARISONS WITH THE PARENT

Plants of the new cultivar 'Sweet Gino' may be distinguished from the seed parent, breeding line 04081-1, by the following combination of characteristics:

1. 'Sweet Gino' initiates blooming after approximately 35 weeks from the planting of a rooted cutting, whereas the seed parent does not flower within the first year after planting.
2. 'Sweet Gino' exhibits a higher degree of sensitivity to gibberellic acid treatment for the induction of blooming, when compared to that of the seed parent.

Plants of the new cultivar 'Sweet Gino' may be distinguished from the pollen parent, breeding line 04094-1, by the following combination of characteristics:

1. The foliage color of 'Sweet Gino' is a lighter shade of green when compared to the foliage color of the pollen parent.
2. The flower of 'Sweet Gino' is smaller than the flower of the pollen parent.
3. 'Sweet Gino' initiates blooming after approximately 35 weeks from the planting of a rooted cutting, whereas the pollen parent initiates blooming after approximately 46 weeks from planting.
4. 'Sweet Gino' exhibits a lower degree of sensitivity to gibberellic acid treatment for the induction of blooming, when compare to that of the pollen parent.

COMPARISONS WITH THE MOST SIMILAR VARIETY OF COMMON KNOWLEDGE

Plants of the new cultivar 'Sweet Gino' may be distinguished from the commercial variety *Spathiphyllum* '54905' (U.S. Plant Pat. No. 13,718) by the following combination of characteristics:

1. 'Sweet Gino' exhibits an unruffled leaf margin, whereas '54905' exhibits heavy ruffling of the leaf margin.
2. 'Sweet Gino' exhibits glossy foliage, whereas the foliage of '54905' is less glossy.
3. 'Sweet Gino' exhibits a foliage color that is darker green when compared to the foliage color of '54905'.
4. The flower of 'Sweet Gino' is larger than the flower of '54905'.
5. The spadix of 'Sweet Gino' exhibits a more rounded apex compared to the spadix of '54905'.
6. 'Sweet Gino' initiates blooming after approximately 35 weeks from the planting of a rooted cutting, whereas '54905' initiates blooming after approximately 24 weeks from planting.
7. 'Sweet Gino' re-blooms infrequently, whereas '54905' re-blooms frequently.
8. 'Sweet Gino' exhibits a low degree of sensitivity to gibberellic acid treatment for the induction of blooming, whereas '54905' exhibits a high degree of sensitivity.

That which is claimed is:

1. A new and distinct variety of *Spathiphyllum* plant named 'Sweet Gino', substantially as described and illustrated herein.

* * * * *